US010420668B2

(12) United States Patent
Klutts (10) Patent No.: US 10,420,668 B2
(45) Date of Patent: Sep. 24, 2019

(54) PATELLA CUP

(71) Applicant: Ossur Iceland ehf, Reykjavik (IS)

(72) Inventor: Zachariah J. Klutts, Irvine, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 707 days.

(21) Appl. No.: 14/946,905

(22) Filed: Nov. 20, 2015

(65) Prior Publication Data

US 2016/0143764 A1 May 26, 2016

Related U.S. Application Data

(60) Provisional application No. 62/082,416, filed on Nov. 20, 2014.

(51) Int. Cl.
*A61F 5/00* (2006.01)
*A61F 5/01* (2006.01)
*A61F 2/64* (2006.01)

(52) U.S. Cl.
CPC .......... *A61F 5/0123* (2013.01); *A61F 5/0106* (2013.01); *A61F 2002/648* (2013.01); *A61F 2005/0176* (2013.01)

(58) Field of Classification Search
CPC ........ A61F 5/0123; A61F 5/0106; A61F 5/01; A61F 5/00; A41D 13/055; A41D 13/0568; A41D 13/0556; A41D 13/06; A41D 13/065; A41D 13/05; A41D 13/00; A63B 71/08; A63B 71/12; A63B 71/1225; A63B 2071/125
See application file for complete search history.

(56) References Cited

U.S. PATENT DOCUMENTS

| | | |
|---|---|---|
| 1,390,915 A | 9/1921 | Loth |
| 2,531,486 A | 11/1950 | Weber |
| 2,883,982 A | 4/1959 | Rainey |
| 3,030,634 A | 4/1962 | Bair |
| 3,099,448 A | 7/1963 | Salvo et al. |
| 3,259,910 A | 7/1966 | Daignault |
| 3,387,305 A | 6/1968 | Shafer |
| 3,669,105 A | 6/1972 | Castiglia |
| 3,779,654 A | 12/1973 | Horne |

(Continued)

FOREIGN PATENT DOCUMENTS

EP  0 941 722 A1  9/1999

OTHER PUBLICATIONS

International Search Report from PCT Application No. PCT/US2015/061755, dated Mar. 22, 2016.

*Primary Examiner* — Victoria J Hicks
(74) *Attorney, Agent, or Firm* — Workman Nydegger (57) ABSTRACT

A patella cup for use with a knee brace includes a main shell secured to a padded liner, and an upper shell disposed above the main shell, and secured at one end to the padded liner. The upper shell may include an extension passing under an upper end of the main shell, so that the upper shell is bendable rearwardly relative to the main shell. A lower strap and at least one upper strap are secured to the padded liner, such that each strap includes an elastic portion to allow each strap to stretch in length when pulled. Loops are secured to the padded liner, on lateral and medial sides of the main shell, with the loops secured to lateral and medial hinges on either side of a knee brace used with the patella cup.

18 Claims, 4 Drawing Sheets

(56) References Cited

U.S. PATENT DOCUMENTS

| | | | |
|---|---|---|---|
| 3,785,372 A | 1/1974 | Craig | |
| 3,817,244 A | 6/1974 | Taylor | |
| 3,900,898 A | 8/1975 | Ackerman | |
| 3,902,482 A | 9/1975 | Taylor | |
| 3,928,872 A | 12/1975 | Johnson | |
| 3,958,569 A | 5/1976 | Vosburgh | |
| 4,068,312 A | 1/1978 | Ledesma | |
| 4,136,404 A | 1/1979 | Lange | |
| 4,169,467 A | 10/1979 | Rabischong et al. | |
| 4,241,730 A | 12/1980 | Helfet | |
| 4,271,831 A | 6/1981 | Deibert | |
| 4,296,744 A | 10/1981 | Palumbo | |
| 4,361,142 A | 11/1982 | Lewis et al. | |
| 4,370,978 A | 2/1983 | Palumbo | |
| 4,372,298 A | 2/1983 | Lerman | |
| 4,381,768 A | 5/1983 | Erichsen et al. | |
| D269,379 S | 6/1983 | Bledsoe | |
| 4,407,276 A | 10/1983 | Bledsoe | |
| 4,423,720 A | 1/1984 | Meier et al. | |
| 4,425,912 A | 1/1984 | Harper | |
| 4,428,369 A | 1/1984 | Peckham et al. | |
| 4,445,505 A | 5/1984 | Labour et al. | |
| 4,487,200 A | 12/1984 | Feanny et al. | |
| 4,489,718 A | 12/1984 | Martin | |
| 4,493,316 A | 1/1985 | Reed et al. | |
| 4,494,534 A | 1/1985 | Hutson | |
| 4,503,846 A | 3/1985 | Martin | |
| 4,506,661 A | 3/1985 | Foster | |
| 4,523,585 A | 6/1985 | Lamb et al. | |
| 4,554,913 A | 11/1985 | Womack et al. | |
| D284,702 S | 7/1986 | Castillo | |
| 4,599,748 A | 7/1986 | Garcia | |
| 4,599,998 A | 7/1986 | Castillo | |
| 4,603,690 A | 8/1986 | Skeen | |
| 4,607,628 A | 8/1986 | Dashefsky | |
| 4,614,181 A | 9/1986 | Karlsson | |
| 4,620,532 A | 11/1986 | Houswerth | |
| 4,621,624 A | 11/1986 | Rayboy | |
| 4,628,916 A | 12/1986 | Lerman et al. | |
| 4,665,905 A | 5/1987 | Brown | |
| 4,681,097 A | 7/1987 | Pansiera | |
| 4,692,946 A * | 9/1987 | Jurga | A63B 71/1225 2/22 |
| 4,697,583 A | 10/1987 | Mason et al. | |
| 4,699,129 A | 10/1987 | Aaserude et al. | |
| 4,715,363 A | 12/1987 | Detty | |
| 4,723,539 A | 2/1988 | Townsend | |
| 4,753,240 A | 6/1988 | Sparks | |
| D298,568 S | 11/1988 | Womack et al. | |
| 4,791,916 A | 12/1988 | Paez | |
| 4,803,975 A | 2/1989 | Meyers | |
| 4,854,308 A | 8/1989 | Drillio | |
| 4,856,501 A | 8/1989 | Castillo et al. | |
| 4,886,054 A | 12/1989 | Castillo et al. | |
| 4,938,207 A | 7/1990 | Vargo | |
| 4,940,044 A | 7/1990 | Castillo | |
| 4,964,402 A | 10/1990 | Grim et al. | |
| 4,986,264 A | 1/1991 | Miller | |
| 4,999,847 A * | 3/1991 | Barcelo | A63B 71/1225 2/22 |
| 5,002,045 A | 3/1991 | Spademan | |
| 5,005,565 A | 4/1991 | Fratesi | |
| 5,024,216 A | 6/1991 | Shiono | |
| D318,736 S | 7/1991 | Castillo | |
| 5,063,916 A | 11/1991 | France et al. | |
| 5,072,970 A | 12/1991 | Dandy, III et al. | |
| 5,107,823 A | 4/1992 | Fratesi | |
| 5,121,742 A | 6/1992 | Engen | |
| 5,131,684 A | 7/1992 | Dandy, III et al. | |
| 5,131,685 A | 7/1992 | Dandy, III et al. | |
| 5,135,469 A | 8/1992 | Castillo | |
| 5,230,697 A | 7/1993 | Castillo et al. | |
| 5,277,697 A | 1/1994 | France et al. | |
| 5,288,287 A | 2/1994 | Castillo et al. | |
| D346,028 S | 4/1994 | Lengyel | |
| D357,070 S | 4/1995 | Castillo | |
| 5,411,037 A | 5/1995 | Hess et al. | |
| 5,417,646 A | 5/1995 | Gauvry | |
| 5,445,602 A | 8/1995 | Grim et al. | |
| 5,500,955 A | 3/1996 | Gongea | |
| 5,554,105 A | 9/1996 | Taylor | |
| D374,746 S | 10/1996 | Skottheim | |
| 5,599,288 A | 2/1997 | Shirley et al. | |
| 5,613,943 A | 3/1997 | Palumbo | |
| 5,641,322 A | 6/1997 | Silver et al. | |
| 5,695,452 A | 12/1997 | Grim et al. | |
| 5,713,837 A | 2/1998 | Grim et al. | |
| 5,716,335 A | 2/1998 | Iglesias et al. | |
| 5,759,166 A * | 6/1998 | Nelson | A61F 5/0118 602/21 |
| 5,759,167 A | 6/1998 | Shields, Jr. et al. | |
| 5,792,084 A | 8/1998 | Wilson et al. | |
| 5,794,261 A | 8/1998 | Hefling | |
| 5,797,864 A | 8/1998 | Taylor | |
| 5,807,294 A | 9/1998 | Cawley et al. | |
| 5,807,298 A | 9/1998 | Palumbo | |
| 5,823,931 A | 10/1998 | Gilmour | |
| 5,865,776 A | 2/1999 | Springs | |
| 5,865,777 A | 2/1999 | Detty | |
| 5,951,504 A | 9/1999 | Iglesias et al. | |
| 6,024,712 A | 2/2000 | Iglesias et al. | |
| D433,756 S | 11/2000 | Castillo | |
| 6,205,583 B1 | 3/2001 | Beland | |
| 6,287,269 B1 | 9/2001 | Osti et al. | |
| D451,644 S | 12/2001 | Fujimoto et al. | |
| 6,393,610 B1 | 5/2002 | Parks | |
| 6,402,711 B1 | 6/2002 | Nauert | |
| 6,436,066 B1 | 8/2002 | Lockhart | |
| D463,886 S | 10/2002 | Cantu, Jr. | |
| 6,540,709 B1 | 4/2003 | Smits | |
| 6,551,264 B1 | 4/2003 | Cawley et al. | |
| 6,553,572 B2 * | 4/2003 | Fiorini | A41D 13/065 2/22 |
| 6,689,080 B2 | 2/2004 | Castillo | |
| 6,793,641 B2 | 9/2004 | Freeman et al. | |
| 6,796,951 B2 | 9/2004 | Freeman et al. | |
| D501,690 S | 2/2005 | Chen | |
| 6,875,187 B2 | 4/2005 | Castillo | |
| D504,981 S | 5/2005 | Vanderhoef | |
| 6,988,999 B1 | 1/2006 | Lin | |
| 7,004,919 B2 | 2/2006 | Gaylord et al. | |
| D517,248 S | 3/2006 | Castillo et al. | |
| 7,011,641 B1 | 3/2006 | Detoro et al. | |
| D518,922 S | 4/2006 | Beland | |
| 7,060,045 B2 | 6/2006 | Mason et al. | |
| 7,083,586 B2 | 8/2006 | Simmons et al. | |
| 7,198,610 B2 | 4/2007 | Ingimundarson et al. | |
| D554,806 S | 11/2007 | Le Carpentier | |
| 7,311,686 B1 | 12/2007 | Iglesias et al. | |
| D588,753 S | 3/2009 | Ingimundarson et al. | |
| 7,597,675 B2 | 10/2009 | Ingimundarson et al. | |
| 7,662,122 B2 | 2/2010 | Sterling | |
| 7,713,225 B2 | 5/2010 | Ingimundarson et al. | |
| 7,749,181 B2 | 7/2010 | Simmons et al. | |
| 7,749,183 B2 | 7/2010 | Ingimundarson et al. | |
| 7,794,418 B2 | 9/2010 | Ingimundarson et al. | |
| 7,806,842 B2 | 10/2010 | Stevenson et al. | |
| 7,819,830 B2 | 10/2010 | Sindel et al. | |
| 7,862,528 B2 | 1/2011 | Scott | |
| 7,867,183 B2 | 1/2011 | Kazmierczak et al. | |
| 7,896,827 B2 | 3/2011 | Ingimundarson et al. | |
| 7,959,590 B2 | 6/2011 | Scott | |
| 9,113,998 B2 | 8/2015 | Romo | |
| 2002/0107462 A1 | 8/2002 | Freeman et al. | |
| 2002/0107464 A1 | 8/2002 | Castillo | |
| 2002/0133108 A1 | 9/2002 | Jagodzinski | |
| 2002/0183674 A1 | 12/2002 | Castillo | |
| 2003/0204156 A1 | 10/2003 | Nelson et al. | |
| 2004/0019949 A1 | 2/2004 | Crockett | |
| 2004/0054307 A1 | 3/2004 | Mason et al. | |
| 2004/0176715 A1 | 9/2004 | Nelson | |
| 2005/0004499 A1 | 1/2005 | Bauerfeind et al. | |
| 2005/0165338 A1 | 7/2005 | Iglesias et al. | |
| 2006/0135903 A1 | 6/2006 | Ingimundarson et al. | |

(56) References Cited

U.S. PATENT DOCUMENTS

| | | |
|---|---|---|
| 2006/0167396 A1 | 7/2006 | Berger |
| 2007/0225824 A1 | 9/2007 | Einarsson |
| 2007/0293798 A1 | 12/2007 | Hu et al. |
| 2008/0072359 A1 | 3/2008 | Godshaw et al. |
| 2008/0139985 A1 | 6/2008 | Gilmour |
| 2008/0195013 A1 | 8/2008 | Ingimundarson et al. |
| 2008/0195015 A1 | 8/2008 | Ingimundarson et al. |
| 2009/0131844 A1 | 5/2009 | Dean et al. |
| 2011/0098618 A1 | 4/2011 | Fleming |
| 2011/0137220 A1 | 6/2011 | Vollbrecht et al. |
| 2013/0172797 A1 | 7/2013 | Merkley et al. |
| 2013/0245523 A1 | 9/2013 | Romo |

\* cited by examiner

PATELLA CUP

FIELD OF THE DISCLOSURE

This disclosure relates to orthopedic braces, and more particularly to a patella cup for protecting the patella (kneecap) of a user's knee, for use with such a brace.

BACKGROUND

Orthopedic braces comprise a broad range of structures and devices used for supporting or stabilizing a joint when worn on the body of a user. Orthopedic braces may serve in either preventative or remedial roles. In the preventative role, the brace can provide additional support, stability and protection to a healthy joint to prevent or minimize injury to the joint due to application of undue stress. In the remedial role, the brace can support and strengthen a weakened joint due to injury or infirmity, and reinforce the joint to prevent further injury, or correct or assist in minimizing effects of the infirmity.

Typically, orthopedic braces include a frame that comprises at least one support member. When there are multiple support members, the brace may include rotational hinges that assist and control movement of the limb. Suitable straps may maintain the brace on the limb, and other features such as pads may relieve pressure of the brace on the limb and surrounding areas.

A predominant orthopedic brace is a knee brace. Knee braces are used to stabilize the knee by preventing excessive movement of the knee, or to facilitate controlled movement of the knee. Many braces comprise a frame having hinges on at least one of the lateral or medial sides of the knee joint. Straps are used to secure the brace to the leg or knee. An injured knee can be fit with an "off the shelf" brace or a "custom-fit" brace, with the selection of the brace depending on the size and shape of an individual's leg.

Many knee braces are designed to reduce knee instability following an injury, fatigue or to treat impairment of the knee, particularly if the knee has damaged ligaments. Braces may be recommended for walking, skiing, running, motocross, or other activities involving twisting, pivoting, or jumping. Besides providing increased stability to the knee, braces may also decrease the risk of injuring the knee or leg, or provide corrective assistance to the knee. One way of protecting the knee is by including attachments such as a patella cup which may be secured onto the brace and configured to cover and protect the patella from impact during physical activities.

While knee braces including a protective patella cup are available, those that are available are often complex, relatively expensive, and/or exhibit problems with fit and comfort, particularly to accommodate twisting, pivoting, and jumping activities such as are common in some physical sports, such as motocross and skiing. Because of these drawbacks, many knee braces and associated patella cups detract from the user's endeavor.

It would be an advance within the art to provide a patella cup for use with a knee brace that is relatively simple in construction, and yet may be easily secured to the knee brace, over the user's patella, while allowing the patella cup to accommodate movements associated with twisting, jumping, pivoting, etc. to maintain the patella cup in the desired position relative to the knee brace and the user's knee as a user participates in a physical activity such as motocross, skiing, or other physical sporting activities involving similar movements.

SUMMARY

According to embodiments of the disclosure, a patella cup for use with a knee brace is provided to shield a patella from debris common to sports like motocross and mountain biking. The patella cup includes a main shell secured to a padded liner, and an upper shell disposed above the main shell, and secured at one end to the padded liner. The upper shell may include an extension passing under an upper end of the main shell, so the upper shell is bendable rearwardly relative to the main shell. A lower strap and at least one upper strap are secured to the padded liner, such that each strap includes an elastic portion to allow each strap to stretch in length when pulled. Loops are secured to the padded liner, on lateral and medial sides of the main shell, with the loops configured to be secured to lateral and medial hinges on either side of a knee brace used with the patella cup.

Details of the embodiments and variations thereof are provided in the following discussion in conjunction with the drawings.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an orthopedic device, and in no way limit the structures or configurations of a simplified polycentric hinge according to the present disclosure.

DETAILED DESCRIPTION OF VARIOUS EMBODIMENTS

A. Overview

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intent is to cover all modifications, alternative constructions, combinations, and equivalents falling within the spirit and scope of the disclosure.

It will be understood that, unless a term is defined to possess a described meaning, there is no intent to limit the meaning of such term, either expressly or indirectly, beyond its plain or ordinary meaning.

The term "front" connotes an outward surface intended to be directed away from a knee of a wearer of the patella cup, and is generally exposed to environmental conditions and protects the knee. The term "rear" connotes an inward surface intended to face a knee of a wearer of the patella cup, and generally placed adjacent to the knee of the wearer and providing cushioning to the knee.

B. Various Embodiments of a Patella Cup for Use with a Knee Brace

Figure 1:
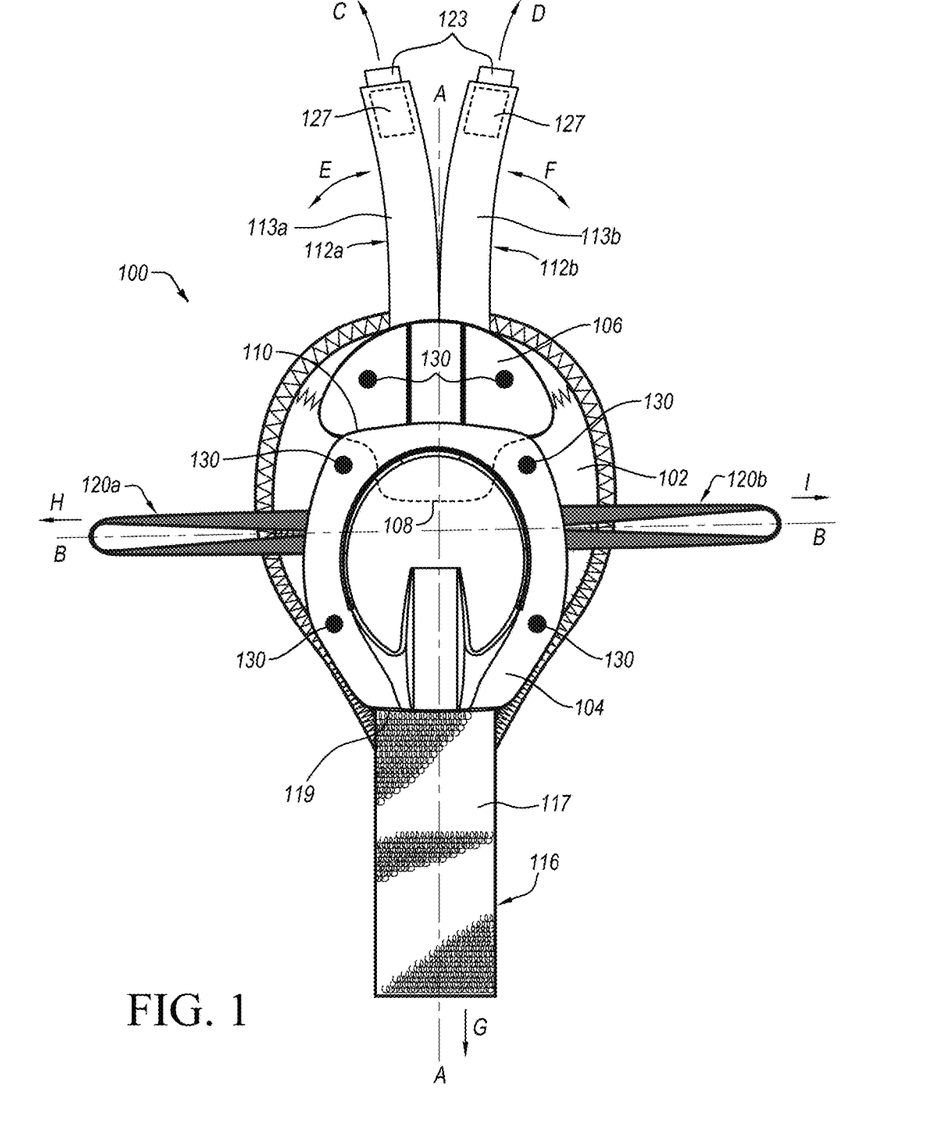
FIG. 1 is a plan view showing the front of a patella cup according to the present disclosure.
Figure 2:
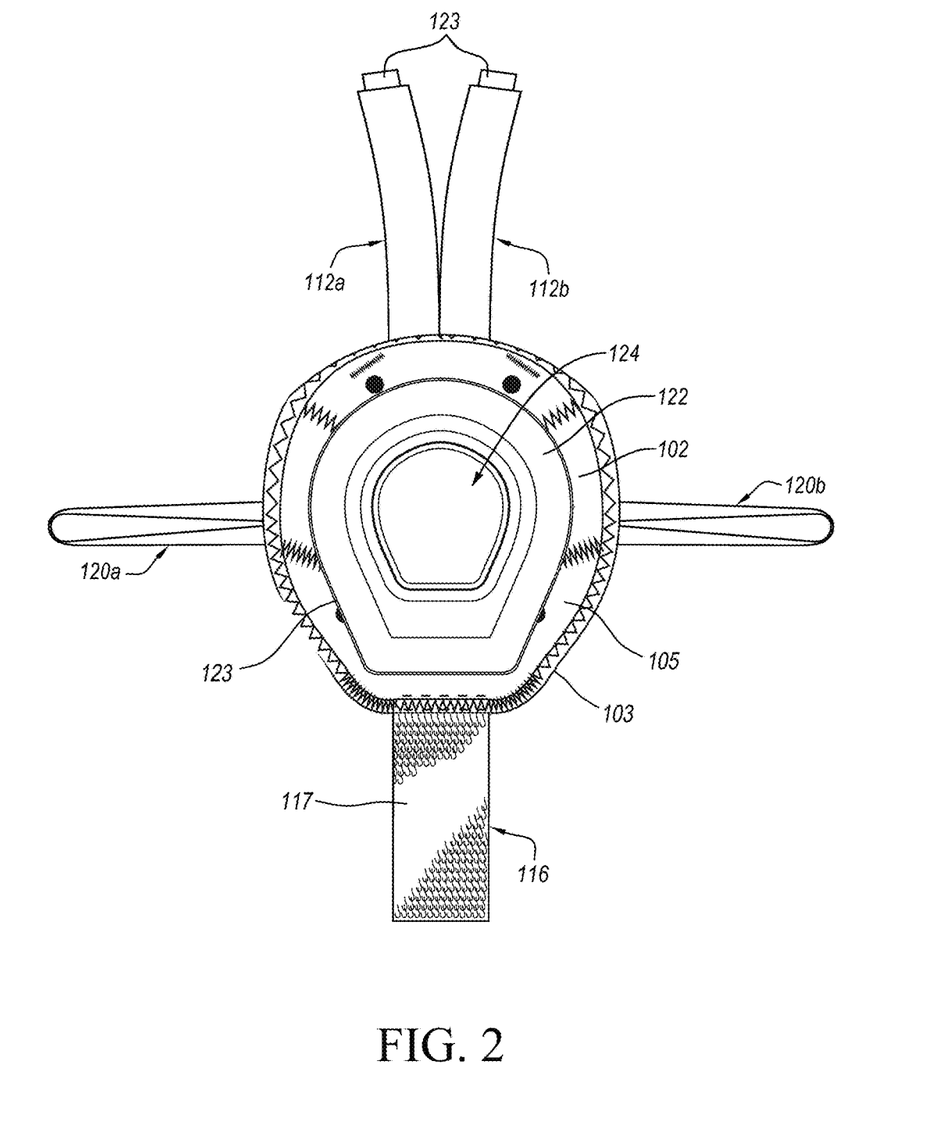
FIG. 2 is a plan view showing the rear of a patella cup according to the present disclosure.

FIGS. 1-2 illustrate an exemplary patella cup 100 according to the present disclosure. FIG. 1 shows a front view of the patella cup 100, while FIG. 2 shows a rear view of the patella cup 100. The patella cup 100 advantageously is configured to be simpler in construction than existing patella cups for use with a knee brace, such as those described and illustrated in U.S. Pat. No. D588,753, granted on Mar. 17, 2009, and U.S. Pat. No. 7,749,183, granted on Jul. 6, 2010, incorporated herein by reference. The above-referenced documents describe known knee braces and patella cups for use therewith. The patella cup may be employed with knee braces such as those described within the above-referenced documents, or other knee braces, and are advantageously simpler in construction and operation than the patella cups described, while providing the ability for the patella cup to accommodate movement of the knee.

The simple construction and operation of the embodiments described is achieved by securing the patella cup to the knee brace via straps that include an elastic portion. Inclusion of an elastic portion allows the strap to maintain the central structure of the patella cup over the knee, while accommodating movement of the knee as the user engages in twisting, pivoting, jumping, and similar movements as are common when engaging in motocross, skiing, or similar sports. Elastic portions of the straps are preferably concealed to avoid catching on objects unassociated with the knee brace. The patella cup is arranged for maintaining continuous protection over the knee of the wearer regardless of flexion or extension of the knee.

The patella cup 100 may include a padded liner 102, a main shell 104, and an upper shell 106 disposed above the main shell 104. The main shell 104 may be configured for placement over the patella of the knee, while the upper shell is preferably disposed above the patella, over the adjacent portion of the femur and quadriceps muscles during use. The main and upper shells 104, 106 maintain a continuous relationship regardless of knee flexion in that there are preferably no exposed gaps between the main and upper shells 104, 106 regardless of knee flexion and extension.

A front surface of the padded liner 102 may be disposed against the rear surface of the main shell 104, with the main shell 104 secured (e.g., riveted) to the padded liner. The upper shell 106 may similarly be secured to the padded liner 102. The upper shell 106 may include an extension 108 extending from a lower portion of the upper shell 106, configured for insertion between an upper end 110 of the main shell 104 and the padded liner 102, so the upper shell 106 is preferably bendable rearwardly (e.g., during knee flexion) relative to the main shell 104 at the extension 108, and thereby preserving the aforesaid continuous relationship and protecting the wearer's knee. The main shell 104 and the upper shell 106 outside of the extension 108 is preferably rigid or semi-rigid.

The patella cup 100 may further include a pair of upper straps 112a and 112b secured to the padded liner 102. Each of the upper straps 112a, 112b may include an elastic portion 114a, 114b (FIG. 3) to allow each upper strap to stretch in length, e.g., when pulled from an upper end thereof. The upper straps 112a, 112b include generally inelastic segments 113a, 113b extending from the elastic portions 114a, 114b, such that the elastic portions 114a, 114b preferably remain concealed by the main and upper shells 104, 106.

While the upper straps 112a, 112b generally extend in a longitudinal direction A of the patella cup 100, the straps 112a, 112b are independently secured to the padded liner 102 and are individually adjustable in generally relative linear directions C, D. The upper straps 112a, 112b may rotate and deviate from the longitudinal direction A, in individual directions E, F toward and away from the longitudinal direction A. The adjustability of the upper straps 112a, 112b enable superior adaptability to known solutions to accommodate a variety of knee brace frame shapes.

A lower strap 116 is secured to padded liner 102, to extend from a bottom of the padded liner 102 and from an opening 119 defined between the padded liner and the main shell 104. The lower strap 116 may include an elastic portion 118 (FIG. 3) to allow the lower strap 116 to also stretch in length, e.g., when pulled from a lower end thereof. A generally inelastic portion 117 extends from the elastic portion 118, and whereby the elastic portion 118 is preferably concealed underneath the main shell 104.

The attachment of the inelastic segment or portion to the elastic segment or portion in either of the upper or lower straps, is preferably arranged so that the elastic segment is substantially underneath and remains underneath the main and upper shells regardless of a stretched or non-stretched configuration. It will be noted however there may be minor deviation in that a small portion of the elastic segment or portion may distend outside of the main and upper shells in a maximum stretched configuration so the elastic segment or portion extends substantially underneath the main and upper shells.

The lower strap 116 generally extends in the longitudinal direction A according to linear direction G, although the lower strap 116 may rotate side-to-side relative to the longitudinal direction A to accommodate the knee brace upon which the patella cup 100 is secured. The opening 119 is preferably sized wider than a width of the lower strap 116 to permit rotation and/or adjustment of the lower strap 116 relative to the patella cup 100.

A pair of loops 120a, 120b may also be secured to the padded liner 102, e.g., with a loop disposed on each lateral side of liner 102, emerging from under the main shell 104 and generally along a generally lateral or side-to-side direction B. For example, the loop 120a may be disposed on a lateral side of the main shell 104 while the loop 120b may be disposed on a medial side of the main shell 104. When the patella cup is placed over the opposite knee, the lateral and medial orientations may be reversed (e.g., where a single patella cup may be suitable for placement over either left or right knees).

The loops 120a, 120b may be looped over lateral and medial hinges, respectively, on either side of a knee brace that the patella cup 100 is to be used with, as described below in FIG. 4. The loops 120a, 120b are preferably individually adjustable on the respective sides and extensible in individual directions H, I generally parallel to the lateral direction B with the ability for some deviation.

As seen in FIG. 2, which shows the rear face of the patella cup 100, (i.e., that surface placed against the user's knee), a padded insert 122 may be placed against a rear surface of padded liner 102, providing further padding and protection to the user's knee during use. Such a padded insert may comprise stretchable, elastic foamed material, such as EVA. The rear surface thereof may be provided with a knee receiving recess 124 formed therein. The rear surface of padded insert 122 may be textured (e.g., including protrusions or dimples formed therein), to aid in retaining insert 122 in place over the knee of the user. Such an insert may be selectively removable from the padded liner 102 of patella cup 100.

The front surface (not shown) of padded insert 122 may include a hook portion of a hook and loop fastener, so the insert 122 may be pressed into the padded liner 102, and be retained where placed. The rear surface of the padded liner 102 may be a fabric material (e.g., brushed fabric loops) to which a hook portion of a hook and loop fastener will adhere, while strips of the hook fastener portion of the fastening mechanism may be glued or otherwise secured to a front surface of the insert 122, allowing the insert 122 to be removably positioned into the padded liner 102, where desired. Although such hook and loop (e.g., VELCRO) fasteners represent one type of fastener mechanism for securing the insert 122 into the padded liner 102, it will be appreciated that other mechanisms may alternatively be employed.

As shown in FIG. 2, the insert 122 has a periphery 123 solely contained within a cavity 105 defined by the padded liner 102. The cavity 105 conforms to an internal shape of the main shell 104 and the upper shell 106. The insert 122 therefore is also preferably fully within the confines of a periphery 103 of the padded liner 102. This arrangement aids in isolating the insert 122 to the anterior aspect of the knee and particularly the patella of a wearer.

Figure 3:
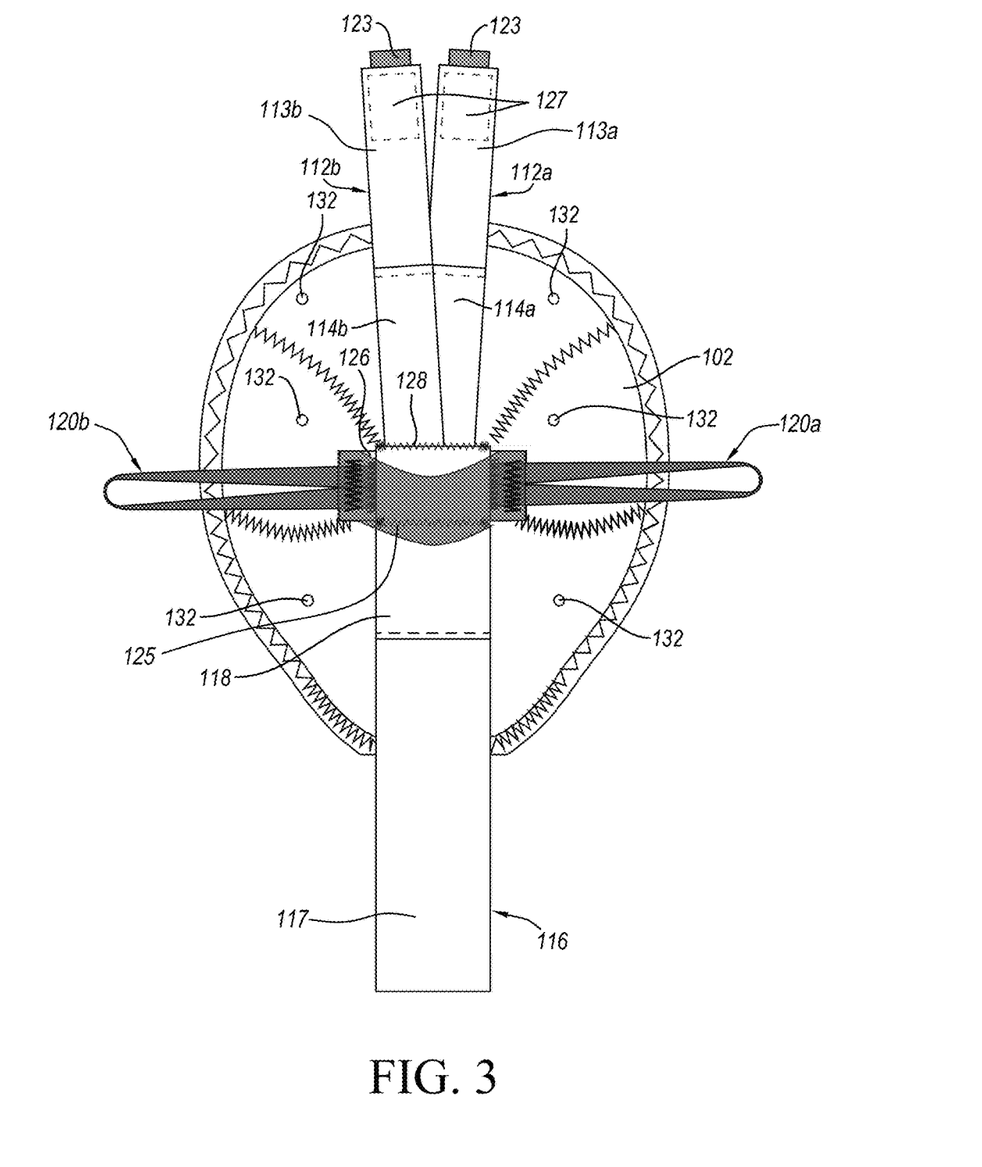
FIG. 3 is a plan view showing construction of the padded liner, upper and lower straps, and the loops for securing the patella cup to hinges of an associated knee brace.

FIG. 3 shows a front view of the patella cup 100, without the main shell 104 and the upper shell 106 (e.g., before they are riveted or otherwise secured to padded liner 102). This view better illustrates the portions of the upper straps 112a, 112b, the lower strap 116, and the loops 120a, 120b that are hidden beneath the main shell 104 and/or the upper shell 106. As seen, the elastic portions 114a, 114b, and 118 of the various straps are preferably covered by the upper shell 106 and/or by the main shell 104 during the extent of usage of the patella cup by a wearer.

According to the described embodiments, only a portion of any strap may be formed of an elastic material, which elastic material can stretch in length when pulled. The inelastic segments 113a, 113b of straps 112a, 112b are formed of any suitable non-elastic fabric material (e.g., 1 inch polyester webbing). Similarly, the inelastic portion 117 of the lower strap 116 is preferably formed of a non-elastic fabric material.

The inelastic portion 117 of the lower strap 116 may include hook material of a hook and loop fastener (e.g., VELCRO) on one surface (e.g., rear surface), and loop material of a hook and loop fastener on the other surface (e.g., front surface). The hook and loop fastener structure of lower strap 116 may provide a simple and effective mechanism for lower strap 116 to be secured to a portion of a knee brace (e.g., a padded, soft guard member) employed with the patella cup 100. The lower strap 116 may be secured to a soft guard member below the knee of such a knee brace, as shown in FIG. 4.

Figure 4:
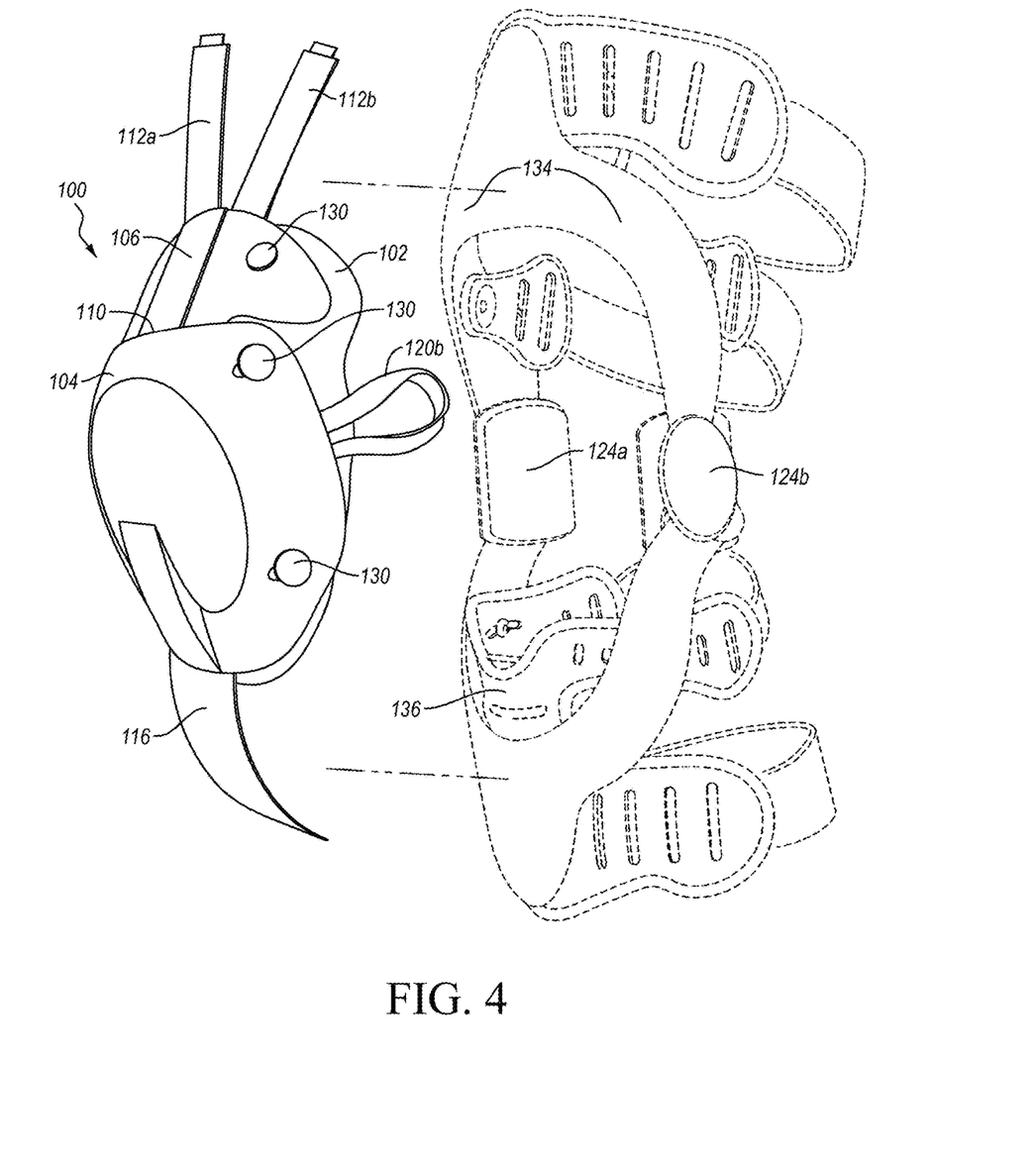
FIG. 4 is a perspective view showing a patella cup according to the present disclosure secured to an associated knee brace.

Similarly, upper straps 112a, 112b may include hook and/or loop fastener material included to provide a simple and effective mechanism for securing upper straps 112a, 112b to the knee brace (e.g., a frame member, soft guard member, etc., located above the knee) employed with patella cup 100, as seen in FIG. 4. As seen in FIGS. 1 and 3, the hook portion of a hook and loop fastener may be stitched or otherwise secured to straps 112a, 112b.

As shown, the upper ends of each strap 112a, 112b may include a ribbon roll (e.g., loop) stitched therein, at 123. Such straps 112a, 112b may be wrapped around a member of the knee brace (e.g., a frame member above the knee), and secured thereto with hook fasteners 127. Alternatively, instead a loop portion of the hook and loop fastener may replace the hook portion 127. In variations, other securing mechanisms (i.e., other than hook and loop fasteners) could alternatively be provided (e.g., snaps, buckles, etc.).

FIG. 3 illustrates how the straps and loops may be secured to the padded liner 102, and which portions of each structure may be formed of the elastic material. This arrangement allows the straps and loops to stretch in length, and the straps and loops of the patella cup to accommodate movement of the knee as the user engages in twisting, pivoting, jumping, etc. The loops 120a and 120b may be secured (e.g., stitched) to a limiter segment 125 which passes over lower strap portion 118.

The limiter segment 125 is attached (e.g., with loops 120a, 120b) to another length of an extension segment 126, which passes under lower strap portion 118. The segments 125, 126 may together form a loop through which lower strap portion 118 is threaded. At least one of the segments 125, 126 may be formed of an elastic material whereas the other segment is preferably inelastic. In an embodiment, the extension segment 126 may be elastic, while the limiter segment 125 may not be inelastic.

In an unstretched condition, the extension segment 126 is preferably shorter in length than the limiter segment 125. When the extension segment 126 is stretched, the limiter segment 125 will inhibit further extension of the extension segment 126 to a predetermined maximum stretched length once the extension segment 126 is stretched to the length of the limiter segment 125, limiting the distance the loops 120a, 120b extend generally along the lateral direction B. The material of loops 120a, 120b themselves may be formed of nylon (e.g., inelastic) or other suitable fabric material.

Such a configuration provides elastic characteristics to the structure to which the loops 120a and 120b are tethered, permitting the loops 120a and 120b to better accommodate movement of the knee during physical activity, while maintaining the patella cup (e.g., particularly the padded liner 102 and the shells 104 and 106) over the user's knee during such movements as twisting, jumping, pivoting, etc.

In an embodiment, the elastic portions 114a and 114b may be stitched or otherwise secured to the padded liner 102 and/or the lower strap portion 118 at the location 128, at or near the top end of the lower strap portion 118. At least in their unstretched condition, all elastic portions of the straps and loops may be hidden beneath the relatively rigid shells 104 and 106. The shells 104 and 106 may be more rigid than the padded liner 102, e.g., being formed of polyethylene or other polyolefin plastic material (e.g., injection molded), while padded liner may be formed of a flexible fabric material. The shells 104 and 106, the underlying padded liner 102, and the insert 122 may absorb impact forces during a crash or similar event, aiding in minimizing transfer of unwanted forces to the user's knee.

Rivets 130 may be provided for securing the relatively rigid main shell 104 and the upper shell 106 to the padded liner 102. As seen in FIG. 1, four rivets 130 may secure the main shell 104, while two rivets 130 (e.g., near a top end of upper shell 106) may secure the upper shell 106 to the padded liner 102. While FIG. 3 shows the front surface of the padded liner 102 before attachment of the main and upper shells 104, 106, respectively, and no rivets 130 are yet present, FIG. 3 shows the location of where the rivets may later be placed, at 132.

The extension 108 may include no rivet or other attachment to padded liner 102 or main shell 104, but may be slid under the upper end 110 of main shell 104 to float and bend according to flexion of the knee. The extension 108 preferably floats underneath the main shell 104 to maintain the continuous covering over the padded liner 102, Because of the flexibility of the padded liner 102 (e.g., formed of a padded fabric material, such as ballistic nylon on the front surface, an unbroken loop brushed tricot knit warp knit on the rear surface, and a polyether polyurethane foam core), and that the upper shell 106 is not directly attached to the main shell 104, the upper shell 106 can bend rearwardly (e.g., during flexion of the knee), to accommodate flexion and extension bending of the user's knee.

FIG. 4 shows a perspective view illustrating an exemplary knee brace which may be employed with the described patella cup 100. As seen, the loops 120a, 120b may be looped around the respective hinges 124a, 124b, further securing the patella cup 100 in place, over the user's knee. Securement is further aided by the straps 112a, 112b, and 116, which may be secured to the frame member 134 and the soft guard member 136, respectively.

While the foregoing embodiments have been described and shown, alternatives and modifications of these embodiments, such as those suggested by others, may be made to fall within the scope of the disclosure. While the orthopedic device has been described in a knee brace, it will be understood that the principles described may be extended to other types of orthopedic devices.

The invention claimed is:

1. A patella cup defining a longitudinal direction and a lateral direction perpendicular to the longitudinal direction, the patella cup comprising:
   a padded liner;
   a main shell disposed against a front surface of the padded liner, the main shell being secured to the padded liner;
   an upper shell disposed along an upper end of the main shell, the upper shell being secured to the padded liner, the upper shell having an extension slidably extending underneath the upper end of the main shell and bendable relative to the main shell such that the main shell and the upper shell maintain a continuous covering over the padded liner;
   a strap system including a plurality of straps extending from underneath the main and upper shells comprising first and second upper straps secured to the padded liner, each of the first and second upper straps including an elastic segment to allow each of the first and second upper straps to stretch in length when pulled from an upper end of each of the first and second upper straps, wherein the elastic segment is located substantially underneath the main and upper shells;
   wherein the first and second upper straps are independently secured to the padded liner and each of the first and second upper straps are individually adjustable in first and second directions, respectively, relative to the longitudinal direction of the patella cup, the first and second upper straps secured to the padded liner and extend in the longitudinal direction of the patella cup, the first and second upper straps are independently secured to the padded liner and are individually adjustable in relative first and second linear directions;
   wherein the strap system includes first and second loops formed from fabric and secured to the padded liner and emerging from under the main shell, the first and second loops extending perpendicularly relative to the longitudinal direction of the patella cup beyond the padded liner in first and second lateral directions along the lateral direction of the patella cup and opposed to one another, respectively, with the first loop disposed on a lateral side of the main shell and the second loop disposed on a medial side of the main shell.

2. The patella cup of claim 1, further comprising a padded insert having an interior surface removably attachable to the padded liner.

3. The patella cup of claim 2, wherein the padded insert defines a knee receiving recess on an exterior surface thereof.

4. The patella cup of claim 3, wherein the exterior surface of the padded insert defines a textured feature.

5. The patella cup of claim 2, wherein the padded insert is located within an entirety of a periphery of the padded liner.

6. The patella cup of claim 1, wherein the strap system includes:
   a lower strap secured to the padded liner and arranged to extend in the longitudinal direction of the patella cup, the lower strap including an elastic portion to allow the lower strap to stretch in length when pulled from a lower end thereof, wherein the elastic segment is located substantially underneath the main and upper shells.

7. The patella cup of claim 6, wherein the lower strap includes the elastic portion confined solely underneath the main and upper shells, and an inelastic portion secured to the elastic portion and extending outside the main and upper shells.

8. The patella cup of claim 6, wherein the lower strap is arranged to rotate side-to-side relative to the longitudinal direction of the patella cup.

9. The patella cup of claim 6, wherein the main shell and the padded liner define an opening through which the lower strap extends, the opening being sized wider than a width of the lower strap and permitting rotation of the lower strap relative to the main shell.

10. The patella cup of claim 1, wherein the first and second loops are inelastic, and are connected at internal ends underneath the main shell by an elastic extension segment by stitching.

11. The patella cup of claim 10, wherein extension of a length of the elastic extension segment is limited by a limiter segment attached thereto.

12. The patella cup of claim 1, wherein the first and second upper straps include the elastic segment confined solely underneath the main and upper shells and an inelastic segment secured to the elastic segment and extending outside the main and upper shells.

13. The patella cup of claim 1, wherein the first and second loops are elastically connected to one another over a predetermined maximum stretched length.

14. The patella cup of claim 1, wherein the strap system further includes:
   at least one lower strap secured to the padded liner and extending generally in the longitudinal direction of the patella cup, the at least one lower strap including an elastic portion to allow the at least one lower strap to stretch in length when pulled from a lower end thereof, wherein the elastic segment is located substantially underneath the main and upper shells; and
   first and second loops secured to the padded liner and extending perpendicularly relative to the longitudinal direction beyond the padded liner in first and second lateral directions opposite one another, with the first loop disposed on a lateral side of the main shell and the second loop disposed on a medial side of the main shell;

wherein each of the first and second upper straps, the at least one lower strap and the first and second loops is individually attached to the padded liner.

15. The patella cup of claim 1, wherein the main shell and the upper shell are separately secured to the padded liner by rivets, such that the extension of the upper shell lacks a rivet connecting the same to the padded liner or the main shell so as to float and bend according to flexion of the patella cup.

16. The patella cup of claim 1, wherein the main shell and the upper shell are only coupled to one another by their individual connection to the padded liner.

17. A patella cup defining a longitudinal direction and a lateral direction perpendicular to the longitudinal direction, the patella cup comprising:

a padded liner;

a main shell disposed against a front surface of the padded liner, the main shell being secured to the padded liner;

an upper shell disposed along an upper end of the main shell, the upper shell being secured to the padded liner, the upper shell having an extension slidably extending underneath the upper end of the main shell and bendable relative to the main shell such that the main shell and the upper shell maintain a continuous covering over the padded liner;

a strap system including a plurality of straps extending from underneath the main and upper shells comprising first and second loops formed from fabric and secured to the padded liner and emerging from under the main shell, the first and second loops extending perpendicularly relative to the longitudinal direction beyond the padded liner in first and second lateral directions along the lateral direction of the patella cup and opposed to one another, respectively, with the first loop disposed on a lateral side of the main shell and the second loop disposed on a medial side of the main shell;

wherein the first and second loops are elastically connected to one another over a predetermined maximum stretched length.

18. A patella cup defining a longitudinal direction and a lateral direction perpendicular to the longitudinal direction, the patella cup comprising:

a padded liner;

a main shell disposed against a front surface of the padded liner, the main shell being secured to the padded liner;

an upper shell disposed along an upper end of the main shell, the upper shell being secured to the padded liner, the upper shell having an extension slidably extending underneath the upper end of the main shell and bendable relative to the main shell such that the main shell and the upper shell maintain a continuous covering over the padded liner;

a strap system including a plurality of straps extending from underneath the main and upper shells comprising a lower strap secured to the padded liner and arranged to extend generally in the longitudinal direction of the patella cup and rotate relative to the longitudinal direction of the patella cup, the lower strap including an elastic portion to allow the lower strap to stretch in length when pulled from a lower end thereof, wherein the elastic portion is located substantially underneath the main and upper shells;

wherein the main shell and the padded liner define an opening through which the lower strap extends, the opening being sized wider than a width of the lower strap and permitting rotation of the lower strap relative to the main shell.

\* \* \* \* \*